United States Patent [19]
Morita et al.

[11] Patent Number: 5,847,668
[45] Date of Patent: Dec. 8, 1998

[54] DEVICE FOR SAMPLING DATA FOR FATIGUE ANALYSIS BY RAINFLOW METHOD

[75] Inventors: Takumi Morita, Saga-ken; Yukitaka Murakami, Fukuoka-ken, both of Japan

[73] Assignee: Fukuoka Kiki Co., Ltd., Saga-ken, Japan

[21] Appl. No.: 791,304

[22] Filed: Jan. 30, 1997

[51] Int. Cl.⁶ .................................................. G06F 5/30
[52] U.S. Cl. ............................................ 341/132; 364/508
[58] Field of Search ................................. 341/155, 132; 364/508; 73/760

[56] References Cited

U.S. PATENT DOCUMENTS 5,531,122  7/1996  Chatham et al. ................. 73/760

FOREIGN PATENT DOCUMENTS 61-28090  6/1986  Japan .

OTHER PUBLICATIONS

"In–situ Measurement of Fatigue LIfe by the Rainflow Method", Nikkei Mechanical Oct. 15, 1979, pp. 69–75 with partial English translation.

Tatsuo Endo et al., "Mechanical Behavior of Materials", vol. I, pp. 371–381, The Society of Materials Science, Japan, 1974.

Masao Takahara, Field Data Acquisition System by "Rainflow Method" And fatigue Life estimation of Automobile, pp. 87–93.

*Primary Examiner*—Marc S. Hoff
*Assistant Examiner*—Peguy Jean Pierre
*Attorney, Agent, or Firm*—Evenson, McKeown, Edwards & Lenahan P.L.L.C.

[57] ABSTRACT

To more accurately and more simply realize data collection and analysis for analyzing fatigue phenomenon of materials by the Rainflow Method, strain signals from a strain detecting means attached to an object for analyzing fatigue is A/D-converted at predetermined intervals, a peak of the A/D-converted strain signal is sampled, the peak value is detected, a valley is sampled, the valley value is detected, the difference between the peak value and the valley value is calculated, count values for respective levels are calculated in accordance with the magnitudes of the differences and the count values at the respective levels are written to a memory card detachably provided to the main body of the device of sampling data.

2 Claims, 5 Drawing Sheets

DEVICE FOR SAMPLING DATA FOR FATIGUE ANALYSIS BY RAINFLOW METHOD

BACKGROUND OF THE INVENTION

1. Field of the Invention

The present invention relates to a device for sampling data for fatigue analysis data in respect to repeated strain of a material, such as metallic materials, polymer materials, ceramics and the like, in which a fatigue phenomenon is caused by a long period of application of repeatedly fluctuating loads, and specifically relates to a technology of data-processing and recording measured strain and its frequency by Rainflow algorithm for analyzing the fatigue phenomenon.

2. Description of Related Art

With regard to fatigue ruptures of metals or other materials of airplanes, vehicles, various machines, plants and buildings, the Rainflow Method has been known as a means for evaluating the influence on fatigue of repeated loads applied on various portions of structures. The Rainflow Method is an algorithm for decomposing and processing waveforms of complicatedly varying stress or strain in correspondence with fatigue phenomena.

The Rainflow Method is described in, for example, "In-situ Measurement of Fatigue Life by the Rainflow Method", NIKKEI MECHANICAL 1979. 10. 15, p.p. 70–76, Endo T. et al., proceedings of the 1974 Symposium on Mechanical Behavior of Materials, vol. 1, p. 371, 1974, or the like.

According to the Rainflow Method, the strain waveform is A/D-converted and a difference P/V between a value P of a peak of the strain waveform and a value V of a valley thereof is calculated and processed based on the Rainflow algorithm, mentioned later, whereby the fatigue damage is calculated.

A monitoring device for fatigue damage based on the principle of the Rainflow Method is disclosed in Japanese Patent Publication No. Sho 61-028090.

The monitoring device is constituted by a sampling unit, an A/D converting unit, a data collection pretreating unit such as input cue, a data analyzing unit for decomposing and synthesizing waveforms and a display unit for displaying fatigue damage from an output resistor by numerical values, whereby the analysis of fatigue phenomenon by the Rainflow Method is realized.

However, the monitoring device disclosed in the publication has the following points yet to be improved.

(1) The device per-se is excessively large, since the same device carries out operations ranging from sampling strain signals to analyzing data and outputting the situation of fatigue damage. Therefore, attachment and installation of the device becomes difficult and measurement of data becomes impossible, depending on the kind of machine to be measured.

(2) The amount of data is enormous, since all the sampled strain signals are stored in a memory, making it difficult to sample data over a long period of time. Further, when the sampling interval is changed, the time period capable of sampling data varies with a memory having the same capacity and therefore, the management of data is difficult to perform.

(3) When the object of monitoring is a rotating body such as a shaft or a wheel, data must be sampled by rotating the detecting unit. However, the device cannot be attached directly to the object for monitoring since the device is large-scale and therefore, transmitting via a slip ring or FM wave is necessary. Accordingly, the reliability of data may be deteriorated by ambient noise.

(4) An enormous amount of processing time is required since extracting P/V values from sampled data and processing steps by complicated calculating formulas for stratifying the P/V values are indispensable for Rainflow processing.

SUMMARY OF THE INVENTION

Hence, it is an object of the present invention to resolve the problems in the conventional device of analyzing fatigue phenomenon by the Rainflow Method, and to more accurately and more simply realize collection and analysis of data for analyzing fatigue phenomena of materials by the Rainflow Method.

According to a first aspect of the present invention, there is provided a device for sampling data for fatigue analysis by the Rainflow Method including means for A/D converting at predetermined intervals a strain signal from a strain detecting means attached to an object for analyzing fatigue, means for sampling a peak of the A/D-converted strain signal and detecting a peak value thereof, means for sampling a valley of the A/D-converted strain signal and detecting a valley value thereof, means for calculating a difference between the peak value and the valley value, means for counting the difference as a number of occurrences of any one of a predetermined plurality of levels in accordance with the amount of difference, a memory card detachably provided to a main body of the device for sampling data including at least the means for A/D converting of the strain signal, the means for detecting the peak value of the strain signal, the means for detecting the valley value of the strain signal, the means for calculating the difference between the peak value and the valley value and the means for counting the difference, and means for writing a value of the difference at each of the plurality of levels on the memory card.

According to a second aspect of the present invention, there is provided a device for sampling data for fatigue analysis by the Rainflow Method according to the first aspect, further including means for storing a value of the A/D-converted strain signal at an initial loading state as a correction value, and means for correcting the A/D-converted strain signal by the correction value in sampling data for fatigue analysis.

According to the Rainflow Method, various steps such as the sampling of the strain signal, extracting P/V values, stratifying the P/V values, calculating fatigue damage and the like are necessary. According to the present invention, by paying attention to the fact that the amount of data is significantly reduced at the point where the P/V values are stratified and the fact that processing up to the stratifying of the P/V values can be realized by comparatively simple algorithms, a circuit carrying out the operations ranging from sampling the strain signal up to stratifying the P/V values is provided in the main body of the device for sampling data for fatigue analysis. Data obtained by stratifying the P/V values is written on the memory card detachably provided on the main body of the data sampling device.

In this way, the device is kept small and light-weight, thus simplifying handling such as attaching and carrying. The device can also be attached also to a rotating body. Furthermore, the amount of data to be stored per unit time is reduced and, accordingly, data can be sampled over a long period of time.

Additionally, the value of the A/D-converted strain signal at the initial loading state is stored as a correction value, and the A/D-converted strain signal is corrected by the correction value in sampling data for fatigue analysis whereby the zero point adjustment is automatically carried out.

DETAILED DESCRIPTION OF THE PREFERRED EMBODIMENT

Figure 1:
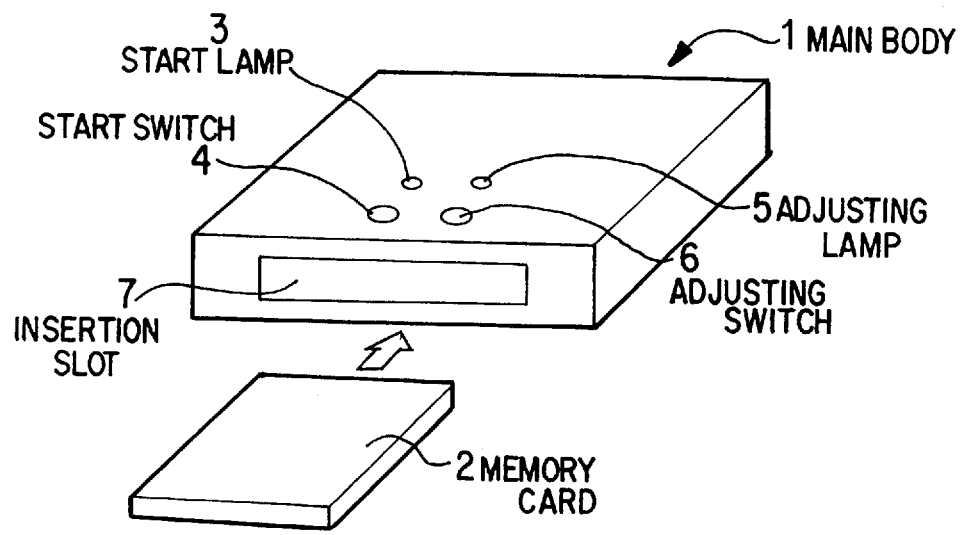
FIG. 1 is an frontal outline perspective view showing an embodiment of a device for sampling data for fatigue analysis in accordance with the present invention.
Figure 2:
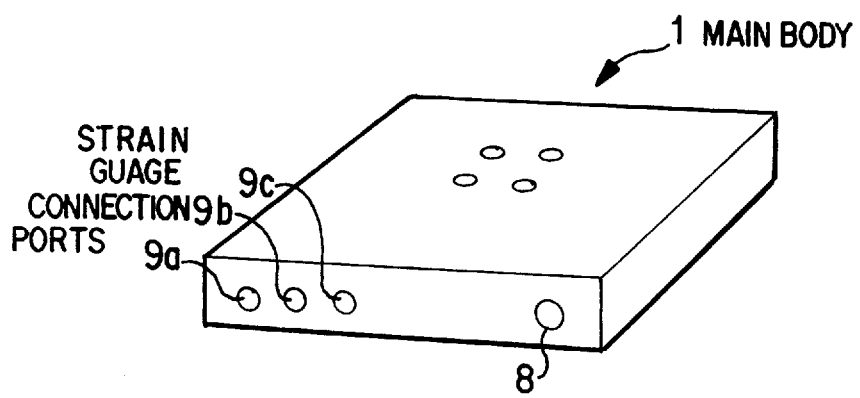
FIG. 2 is an rear outline perspective view showing the device for sampling data for fatigue analysis of FIG. 1.

FIG. 1 is a frontal outline perspective view showing an embodiment of a device for sampling data for fatigue analysis in accordance with the present invention. FIG. 2 is a rear outline perspective view showing the device of sampling data for fatigue analysis of FIG. 1.

The device for sampling data for fatigue analysis is constituted by a main body 1 of said device and a memory card 2 comprising SRAM (Static Random Access Memory) detachably mounted on the main body 1 of said device. As illustrated by FIG. 1, a start switch 4 instructing the starting of measurement, a start lamp 3 showing the starting of measurement, a zero point adjusting switch 6 adjusting the zero point of a strain gage, mentioned later, a zero point adjusting lamp 5 showing the completion of the zero point adjustment etc. are provided on the top of the main body 1 of the device for sampling data for fatigue analysis. A card insertion slot 7 for inserting the memory card 2 is provided at the front of the main body 1 of the device of sampling data for fatigue analysis. Further, as illustrated by FIG. 2, a power source supply port 8 for supplying a power source voltage, strain gage connection ports 9a, 9b and 9c for connecting strain gages, mentioned later, and the like are provided at the back of the main body 1 of the device for sampling data for fatigue analysis.

Figure 3:
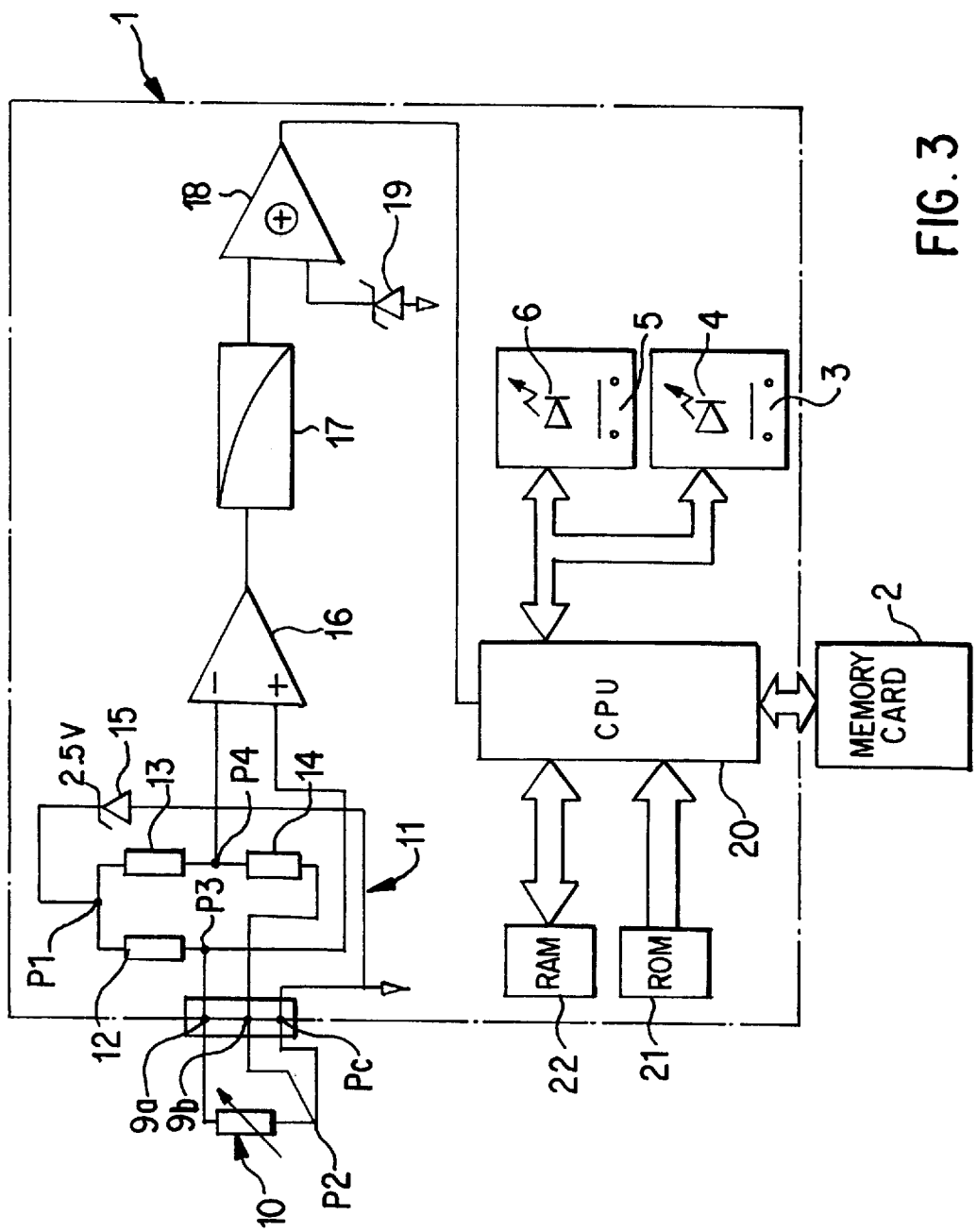
FIG. 3 is a block diagram showing an electric circuit of the device of sampling data for fatigue analysis illustrated by FIG. 1 and FIG. 2.

FIG. 3 is a block diagram showing an electric circuit of the device of sampling data for fatigue analysis illustrated by FIG. 1 and FIG. 2. A 3-line type strain gage 10 is connected to the strain gage connection ports 9a, 9b and 9c. The strain gage 10 constitutes one arm of a bridge circuit 11. That is, a bridge is constituted by the strain gage 10, a resistor 12, a resistor 13 and a resistor 14 and a constant voltage stabilized by a constant voltage element 15, for example, 2.5 V is applied between a connection point P1 connecting the resistor 12 and the resistor 13 and a connection point P2 connecting the strain gage 10 and the resistor 14. The resistance values of the resistors 12, 13 and 14 are selected to be substantially equal to the resistance value of the strain gage 10 at no load and the electric potential of a connection point P3 connecting the resistor 12 and the strain gage 10 is substantially equal to the electric potential of a connection point P4 connecting the resistor 13 and the resistor 14.

Output from the connection point P2 is supplied to a positive input terminal of a differential amplifier 16 and an output from the connection point P4 is supplied to a negative input terminal of the differential amplifier 16. As mentioned above, when the strain gage 10 is at no load, the electric potentials of both of the input terminals of the differential amplifier 16 are substantially equal to each other and therefore, an output of the differential amplifier 16 becomes zero and when pressure is applied on the strain gage 10, and an output having a level in accordance with the pressure is generated. The output of the differential amplifier 16 indicates the strain signal representing the amount of strain. The output from the differential amplifier 16 is supplied to one input terminal of an adder 18 via a low pass filter 17 for removing noise. Also, a constant voltage is supplied from a constant voltage element 19 to the other input element of the adder 18. The input signal changing positively or negatively interposing the zero point is converted to an output signal having one polarity by the adder 18 whereby it can be processed by an A/D converter, mentioned later.

The output from the adder 18 is inputted to an analog port of a CPU (Central Processing Unit) 20. CPU 20 incorporates an A/D converter whereby an analog signal inputted to the analog port is converted into a digital signal and is processed in CPU 20. ROM (Read Only Memory) 21 in which programs etc. are written, and RAM (Random Access Memory) 22, which is used as a working area etc., are connected to CPU 20 via busses. Also, the start switch 4, the start lamp 3, the zero point adjusting switch 6 and the zero point adjusting lamp 5 illustrated by FIG. 1 are connected to CPU 20 via a bus. Furthermore, the memory card 2 is attachably and detachably connected to CPU 20 via a socket.

To the power source supply port 8 of the above-described main body 1 of the device of sampling data for fatigue analysis, an AC adapter, not illustrated, is connected at locations where a commercial power source is available and a battery, not illustrated, is connected at locations where a commercial power source is not available utilized. Incidentally, electric current supply routes to the constant voltage elements 15 and 19 are not illustrated in FIG. 3.

Next, an explanation will be given of the operation of the above-described device of sampling data for fatigue analysis.

First, the strain gage 10 is attached to the object of measurement and is brought into a state of no load or a state where a predetermined initial pressure is applied on the gage. Incidentally in this specification, both states are referred to as the initial loading state.

Figure 4:
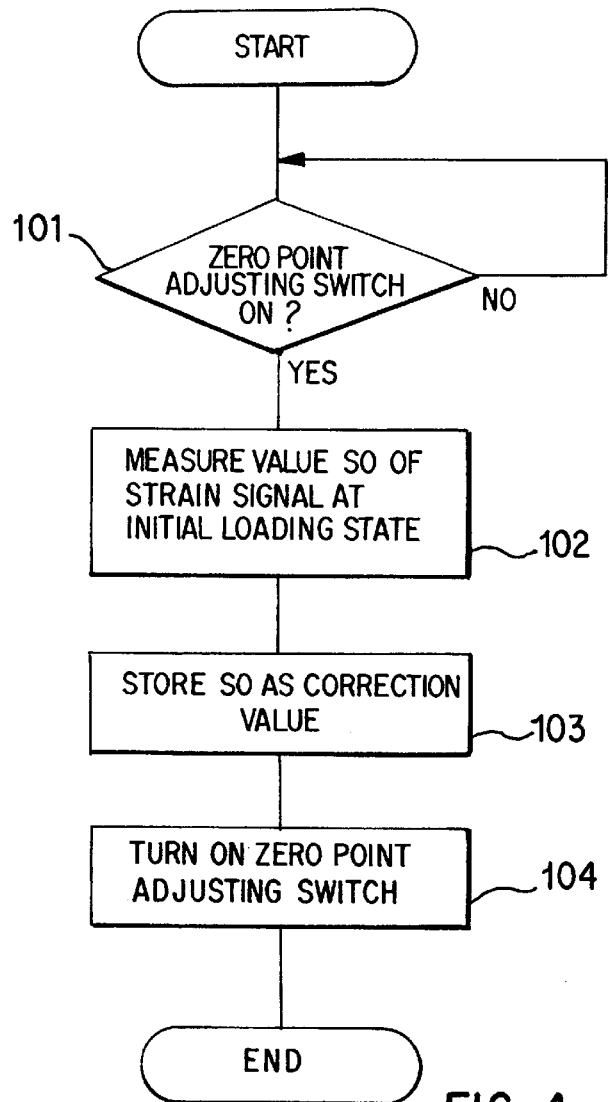
FIG. 4 is a flowchart showing the processing of zero point adjustment.

Next, the zero point adjustment is carried out. FIG. 4 is a flowchart showing processing of the zero point adjustment.

When the zero point adjusting switch 6 is pushed (step 101), CPU 20 measures a value of the strain signal currently supplied from the adder 18 to CPU 20, that is, a value S0 of the strain signal under the initial loading state (step 102), and determines a correction value C so that the value of S0-C becomes zero when the correction value is set to C. That is, C=S0. Next, S0 is stored in RAM 22 as correction value C (step 103). For the operation thereafter, various calculations are carried out based on a value (S1−C) that is produced by subtracting the correction value C from a value S1 of the current strain signal from the adder 18 or a value S2 of the strain signal. The zero point adjustment of the strain gage 10 can automatically be carried out through software by the above described correction processing. When the processing of the zero point adjustment is finished, the zero point adjusting lamp 5 is turned on (step 104), which informs the user that the zero point adjustment has been finished.

Figure 6:
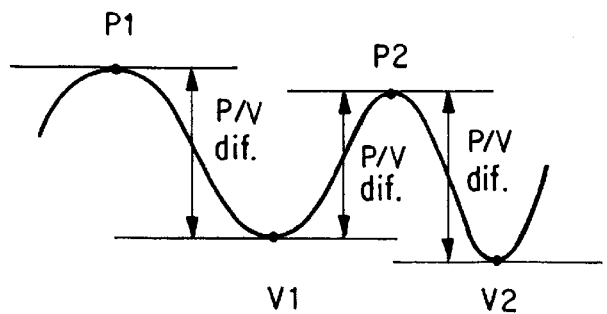
FIG. 6 is an explanatory view for explaining calculation of the P/V difference.
Figure 5:
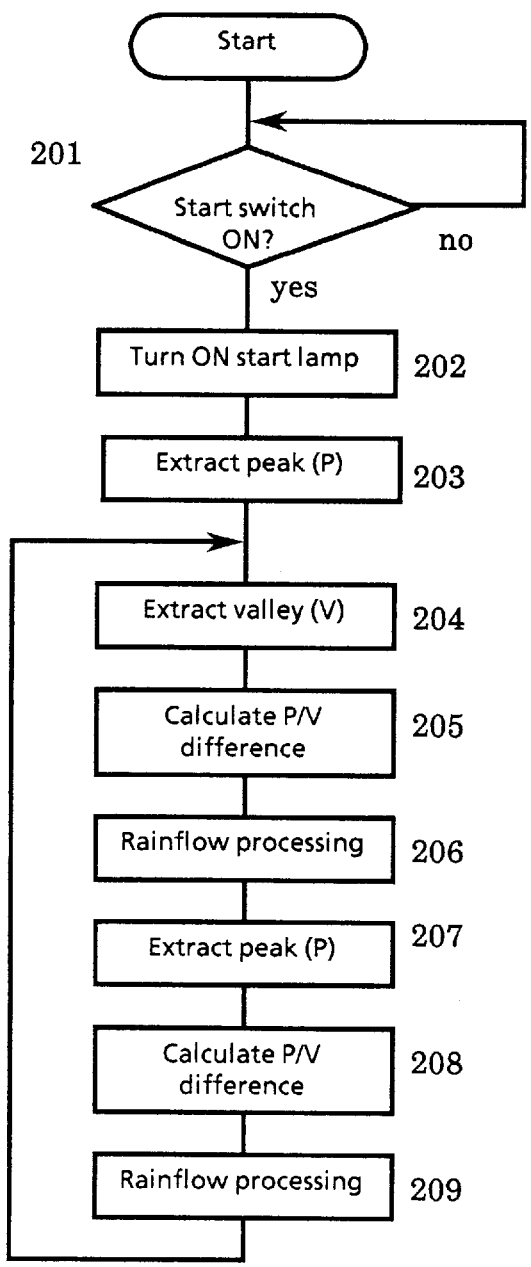
FIG. 5 is a flowchart showing the processing of sampling data for fatigue analysis.

Next, the sampling of data for fatigue analysis is carried out. FIG. 5 is a flowchart showing the processing of sampling data for fatigue analysis. Further, FIG. 6 is an explanatory view for explaining the calculation of P/V differences.

When the start switch 4 is pushed (step 201), the start lamp 3 is turned on (step 202) thereby informing the user that the measurement has started. Next, CPU 20 samples strain signal data by sampling the value S2 of the strain signal at constant periods. CPU 20 extracts a peak of the strain signal (for example, P1 shown by FIG. 6) (step 203) and records the peak value P. Next, CPU 20 extracts a valley of the strain signal (for example, V1 shown by FIG. 6) (step 204) and records the valley value V. Next, CPU 20 calculates an absolute value for the difference between the peak value P and the valley value V ($|P-V|$) (hereinafter, referred to as P/V difference) (step 205). The Rainflow processing, mentioned later, is carried out based on the data of the P/V difference (step 206). Next, a succeeding peak (for example, P2 shown by FIG. 6 ) is extracted (step 207) and the peak value P is recorded. Next, the P/V difference is calculated (step 208) and the Rainflow processing is carried out based on the data of the P/V difference (step 209). Then the operation returns to step 204, samples a succeeding valley (for example, V2 shown by FIG. 6) and records the valley value V. In the following, the above-described operation is repeated.

Figure 7A:
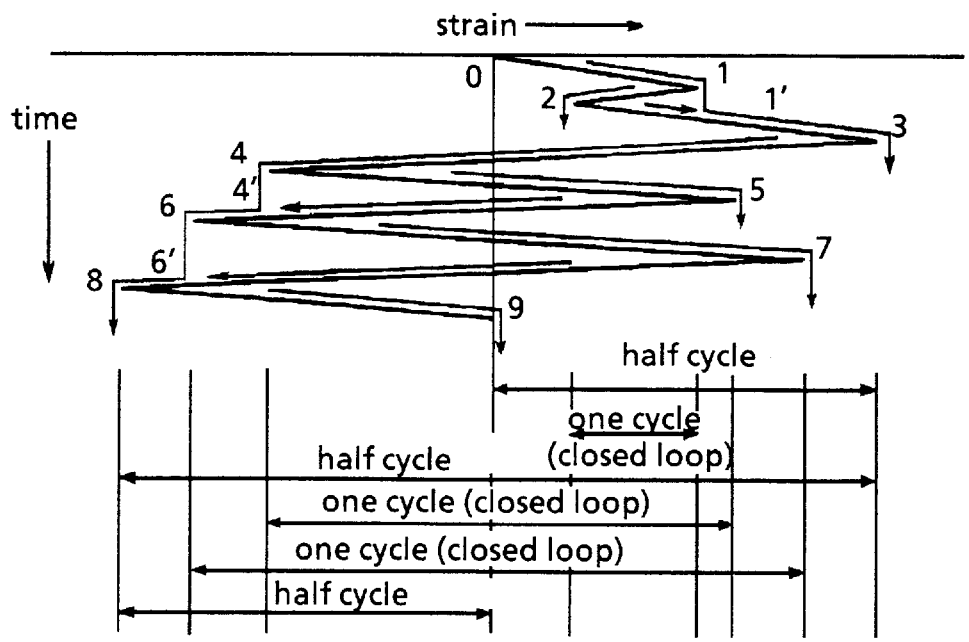
FIGS. 7A and 7B illustrate graphs for explaining the Rainflow Method.
Figure 7B:
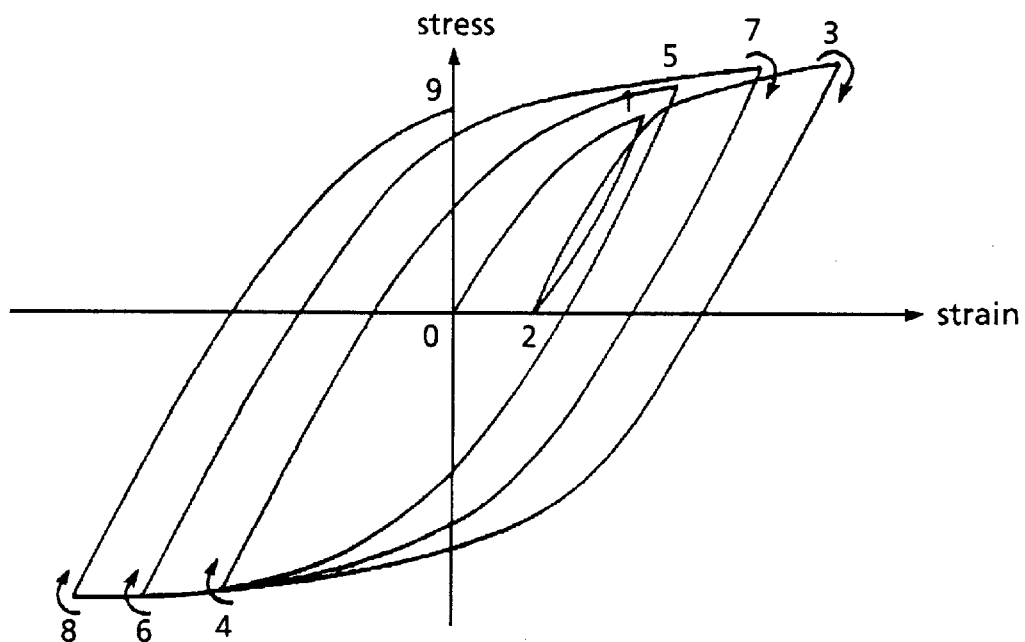

Here, a simple explanation will be given of the Rainflow Method. FIGS. 7A and 7B are graphs explaining the Rainflow Method. FIG. 7A indicates the relation between time and strain and FIG. 7B indicates the relation between strain and stress.

The decomposition of waveforms by the Rainflow Method is executed by the following procedure.

Firstly, the time axis is set vertically and a change over time of the strain to be decomposed is regarded as a multiplexed roof structure 1-2-....-9 as illustrated by FIG. 7A. Imagine that a raindrop is made to flow in the order of the number of peaks and valleys from the position of the root of each roof of a multiplexed roof structure. A raindrop falls and is stopped satisfying the following three conditions. Further, a strain amplitude effective to fatigue is constituted by measuring horizontal coordinates through which a raindrop flows until it stops, and by decomposing a strain width having a size corresponding thereto.

[Condition 1] A raindrop starts to flow in the order of the numbers from the top of a roof and continues falling down to lower roofs until one of stopping conditions is satisfied.

[Condition 2] (Stopping conditions) A rain drop that is falling from an eave stops falling when one of the following two conditions is satisfied.
  a) In the case of rightward flowing: an eave of another roof is present on the left side of a start point of the raindrop flowing rightwardly.
  b) In the case of leftward flowing: an eave of another roof is present on the right side of a start point of the raindrop flowing leftwardly.

For example, according to FIG. 7A, with regards to a flow to the right from a point 6, the raindrop falls at the eave of a point 7. However, an eave 8 is present on the left side of the starting point 6 and accordingly, the raindrop stops flowing at a time during which it is falling from the eave 7.

[Condition 3] When a raindrop is already flowing at a portion of a roof, the flow of another raindrop is stopped at that portion. For example, the flow of a raindrop on a roof 5–6 with a point 5 as the starting point reaches a point 4' and is stopped there.

In this way the waveform is decomposed from the model of the flow of the raindrop, whereby the strain amplitudes are determined. Here, the information of the change over time of the strain is processed by disregarding all of the time-sequential procedure among peaks and valleys. As a result, the strain amplitudes (P/V differences) and the frequencies of these are sampled by considering only the sizes of peaks and valleys and the order of occurrences of these.

When the strain waveform is decomposed by the Rainflow algorithm, the fatigue damage rate corresponding to each one of the strain amplitudes can be calculated by using the relation of Coffin-Manson, or the conventional relation of S (Total strain width value)/N (Number of time until rupture) or the like. Further, the accumulated fatigue damage rate with the time of starting measurement as an onset is provided by successively adding the fatigue damage rates which are calculated at each time of inputting the strain waveforms. According to Minor's law, the point where the accumulated fatigue damage rate reaches 100% can be regarded as the theoretical point where the rupture occurs. Therefore, the prediction of the fatigue is made possible.

As described above, a simple explanation has been given of the Rainflow Method. According to the above-described Rainflow Method a plurality of levels in accordance with the magnitudes of the P/V differences are prepared and when the P/V difference occurs, it is counted as a number of occurrences to one of the predetermined plurality of levels in accordance with the magnitude of the P/V difference. The count values at respective levels are written on the memory card 2.

Accordingly, it is not necessary in this embodiment to store all the sampling values of the strain signals provided from the strain gage 10 but the count value for each level is written to the memory card 2 when the P/V difference occurs. Therefore, the amount of data written on the memory card 2 is significantly reduced. Thereby, data necessary for measuring fatigue for a longer period of time can be sampled in respect of the memory card 2 having the same capacity.

Additionally, the memory card 2 may be periodically interchanged and removed from the device for sampling data for fatigue analysis, and may be connected to a personal computer etc. provided at another location, where the fatigue damage rate can be calculated based on the data in the memory card 2, that is, the count values for the respective levels.

The following effects are achieved by the present invention.

(1) The amount of data to be stored per unit time is reduced and therefore, data can be sampled over a longer period of time.

(2) The steps up to stratifying the P/V values in Rainflow processing are carried out by a data sampling device and therefore, not only the calculation is simplified but the circuit is simplified. Thereby, the power consumption of the device is reduced and continuous measurement can be carried out over a longer period of time by using a battery on the market.

(3) The entire device can be made to be small and light-weight and therefore, it can be attached to a rotating body or operating machines and structures.

(4) The fatigue damage rate can be calculated by using a personal computer etc. provided at another location, by using the memory card.

(5) The zero point adjustment can automatically be carried out by storing the value of the A/D-converted strain signal at an initial loading state as correction value and by correcting the A/D-converted strain signal by the correction value in sampling data for fatigue analysis.

What is claimed is:

1. A device for sampling data for fatigue analysis by the Rainflow Method, comprising:

means for A/D converting at predetermined intervals a strain signal from a strain detecting means attached to an object for analyzing fatigue;

means for sampling a peak of the A/D-converted strain signal and detecting a peak value thereof;

means for sampling a valley of the A/D-converted strain signal and detecting a valley value thereof;

means for calculating a difference peak value and the valley value;

means for counting the difference as a count value representing a frequency of occurrences of any one of a predetermined plurality of levels in accordance with an amount of the difference;

a memory card detachably provided to a main body of the device for sampling data including at least the means for A/D converting the strain signal, the means for detecting the peak value of the strain signal, the means for detecting the valley value of the strain signal, the means for calculating the difference between the peak value and the valley value and the means for counting the difference; and means for writing said count value of the difference at each of the plurality of levels on the memory card.

2. The device for sampling data for fatigue analysis by the Rainflow Method according to claim 1, further comprising:

means for storing a value of the A/D-converted strain signal at an initial loading state as a correction value; and means for correcting the A/D-converted strain signal by the correction value in sampling data for fatigue analysis.

* * * * *